United States Patent [19]

Fowlkes

[11] Patent Number: 4,967,001

[45] Date of Patent: Oct. 30, 1990

[54] ALKYLATION OF TOLUENEDIAMINE AND PARA-PHENYLENEDIAMINE WITH ISOBUTYLENE IN THE PRESENCE OF ACIDIC, CRYSTALLINE MOLECULAR SIEVES

[75] Inventor: Robert L. Fowlkes, Milton, Fla.

[73] Assignee: Air Products and Chemicals, Inc., Allentown, Pa.

[21] Appl. No.: 213,659

[22] Filed: Jun. 30, 1988

[51] Int. Cl.$^5$ .................. C07C 205/00; C07C 207/00; C07C 45/00

[52] U.S. Cl. ..................................... 564/305; 564/409

[58] Field of Search ................................ 564/409, 305

[56] References Cited

U.S. PATENT DOCUMENTS 3,670,030  6/1972  Sparks ................................ 564/409
4,745,223  5/1988  Burgoyne, Jr. et al. ............ 564/305

FOREIGN PATENT DOCUMENTS 0202557  11/1986  European Pat. Off. ............ 564/409
0226781   1/1987  European Pat. Off. ............ 564/409
0414574   8/1922  United Kingdom ................ 564/409

*Primary Examiner*—Richard L. Raymond
*Assistant Examiner*—Raymond Covington
*Attorney, Agent, or Firm*—Russell L. Brewer; James C. Simmons; William F. Marsh

[57] ABSTRACT

This invention relates to an improvement in a process for producing tert-butyl-derivatives of aromatic amines, e.g., para-phenylenediamine and toluenediamine by the reaction of isobutylene with the corresponding aromatic diamine in the presence of a highly acidic crystalline alumino-silicate catalyst. The improvement constitutes adding sufficient water to the catalyst to provide at least partial saturation of the catalyst during the reaction.

12 Claims, No Drawings

ALKYLATION OF TOLUENEDIAMINE AND PARA-PHENYLENEDIAMINE WITH ISOBUTYLENE IN THE PRESENCE OF ACIDIC, CRYSTALLINE MOLECULAR SIEVES

TECHNICAL FIELD

This invention pertains to an improved process for alkylating toluenediamine and para-phenylenediamines in the presence of crystalline molecular sieve catalysts.

BACKGROUND OF THE INVENTION

Processes for alkylating a variety of alkylatable aromatic compounds by contacting such compounds with a hydrocarbon radical providing source such as an olefin or alcohol are widely known. Typically, alkylatable aromatic compounds are mononuclear aromatic compounds themselves or those substituted with a hydroxyl, amine or an ether group. The alkylation has been carried out in the presence of homogeneous and heterogeneous catalyst systems.

Representative references which illustrate some of the early processes in forming ring alkylated aromatic amines are:

British Patent No. 414,574 discloses the reaction of aniline with various olefins, e.g., cyclohexene and alcohols. e.g.. butanol in the presence of a neutral or weakly acidic catalyst system commonly referred to as hydrosilicates at temperatures from 200-270° C. Ortho and para-cyclohexylaniline. N-cyclohexylaniline. N-butylaniline and para-methyl-ortho-cyclohexylaniline and N-cyclohexyl-para-toluidine are listed as representative products.

British Patent No. 846,226 discloses ring alkylation of aromatic amines with olefins using active, substantially neutral bleaching earths of the montmorillonite type as a catalyst.

AS 1,051,271 discloses the ring alkylation of aniline with an olefin. e.g., ethylene, in the presence of kaolin or in the presence of aluminum and aluminum alloys. Alkylation with higher olefins, e.g., propylene. butylene, etc., was carried out in the presence of Friedel-Crafts catalysts or bleaching earths under liquid phase conditions at temperatures from 150-350° C. Representative examples of operable catalytic systems including aluminum chloride, zinc chloride, boron trifluoride, sulfuric acid. phosphoric acid and bleaching earth. Ring alkylation at the ortho-position was predominant, although other products such as the di and tri-alkylated aniline product were produced.

Netherlands Application No. 6,407,636 has recognized that alkylation of various aromatic and heterocyclic compounds can be carried out in the presence of a zeolite having a pore size from 6-15 Angstroms wherein active cationic sites are obtained with an exchangeable metal or hydrogen cations in their ordered internal structure. Alkylating agents include olefins having from 1 to 12 carbon atoms, alkyl halides such as propyl bromide and ethyl chloride., and alkanols, such as, methanol, ethanol, and propanol. Various compounds were suggested as being suited for alkylation and these include both the heterocyclic and aromatic ring compounds. For aromatic amine alkylation it was suggested that a zeolite with a disperse distribution of acidic sites should be utilized. It was believed the highly acidic zeolite catalysts which have a high density of acidic sites may bind the amine to the catalyst and block the pore structures. In Example 1, aniline was alkylated with propylene using sodium zeolite X having a pore size of 13 Angstroms and numerous alkylated amines were produced. Example 3 shows alkylation of diphenylamine with cyclohexene using a rare earth exchanged 13 X zeolite. Again, numerous ring alkylated products were produced and high temperatures, e.g., 300° C. and above apparently being required to weaken the amine-acid bond.

French Patent No. 1,406,739, which is equivalent to Netherlands Application No. 6,407,636, discloses the preparation of alkylated aromatic compounds having polar substitutions thereon utilizing alumino-silicates having a pore size of at least 6 Angstroms as a catalyst. Cations of low valence were deemed to have been particularly effective for the ring alkylation of aromatic compounds having weakly basic substituents such as aromatic amines. The examples show the alkylation of aniline with propylene in the presence of a sodium zeolite X and alkylation of diphenylamine with propylene in the presence of a molecular sieve 13X which has undergone a partial exchange with rare earth metals and having a pore size of 13A°.

U.S. Pat No. 4,745,223 discloses the preparation of tert-alkyl toluenediamines and other aromatic amines by reacting an olefin with an aromatic amine in the presence of a highly acidic crystalline alumino-silicate. Examples of aromatic diamines include tert-butyl-toluenediamine.

U.S. Pat. No. 3,670,030 discloses the alkylation of a phenolic compound with an olefin in contact with an alumina catalyst. To prevent deactivation of the catalyst, water was added to the reaction zone in a controlled amount. e.g., from about 500–3000 ppm based upon the phenolic compound.

U.S. Pat. No. 3,546,100 shows a process for cracking hydrocarbon feedstocks over a rare earth exchanged crystalline alumina-silicate catalyst. Water addition to the reaction was made in order to control catalyst activity.

SUMMARY OF THE INVENTION

This invention pertains to an improved process for effecting alkylation of an aromatic diamine, i.e., toluenediamine and para-phenylenediamine with isobutylene. The basic process comprises contacting the aromatic diamine with isobutylene in the presence of an acidic crystalline alumno-silicate catalyst under conditions for effecting alkylation. The improvement comprises contacting the catalyst with water in sufficient amount to at least partially saturate the catalyst.

Some of the advantages associated with this invention include:

p an ability to effect and maintain alkylation at high conversion;

p an ability to effect and maintain ring alkylation at high rates;

p an ability to minimize formation of dialkylated toluenediamine by-products;

p an ability to utilize a fixed bed catalytic reactor lending itself to continuous vapor or liquid phase operation; and p an ability to retard catalyst deactivation and operate over several cycles in batch operation or over substantial periods in fixed-bed operation without catalyst regeneration .

DETAILED DESCRIPTION OF THE INVENTION

As stated above, crystalline alumino-silicates deactivate in the alkylation of certain aromatic diamines, these being toluenediamine and para-phenylenediamine and the alkylation is carried out with specific olefins; e.g., isobutylene. In some cases, catalyst deactivation occurs with other olefins although the catalyst does not respond with water treatment to be described; and in other cases, the aromatic amines, e.g., meta-phenylenediamine do not deactivate rapidly as does para-phenylenediamine or toluenedamine in the reaction with isobutylene. However, deactivation may occur with the alkylation of meta-phenylenediamine on reaction with cyclopentadiene but the catalyst does not respond with water treatment.

In the alkylation of aromatic amines used in this invention, toluenediamine and para-phenylenediamine, the olefin to amine molar ratios will range from about 1 to 20 moles olefin per mole of the aromatic amine and preferably about 2-4 moles olefin per mole of the aromatic amine.

The catalysts useful in the reaction of the present invention are those crystalline molecular sieves which are solid phase and have an acidity factor of at least 0.30 and preferably at least 1 and referred to in U.S. Pat. No. 4,740,620 and are incorporated by reference. More specifically, these highly acidic molecular sieves have sufficient catalytic activity to effect ring-alkylation of the aromatic amine in high conversion (based upon amine) and in high selectivity. The crystalline molecular sieves include crystalline alumino-silicates, commonly referred to as zeolites, and they can be of both natural and synthetic material. Some of the zeolites are faujasite and mordenite. When initially prepared, the cation in the crystalline alumino-silicate usually s an alkali metal, typically sodium. This ion must be exchanged in sufficient proportion, generally in excess of 60%, with an acidic ion such as a rare earth metal, e.g. lanthanum, cerium, praseodymium; hydrogen or some of the transition metals such as nickel, copper, chromium and the like for the practice of this invention. The substitution of various ions for the sodium ion alters the acidity of the zeolite thus making it more reactive and catalytically effective for ring alkylation of the aromatic amine.

The naturally occurring and synthetic zeolites normally have a silica to alumina molar ratio of from 2 to 15:1. The acidity of the zeolite may be altered by a technique called dealumination. In effect, the practice of dealumination decreases the alumna ratio. The removal of alumina from the internal structure can also enlarge the cage structure or pore size of the zeolite to permit entry of and diffusion of larger molecules into its internal structure. It can also have a tendency to increase catalyst acidity. Thus, one may be able to utilize a particular cation in a dealuminated zeolite but not use the same cation in its non-dealuminated counterpart since that catalyst would not meet the acidic requirements of this invention. Some of the techniques for dealumination include chelation, dehydration or acidification, the latter which entails the treatment of the zeolite with an inorganic acid. Such techniques for dealumination of zeolite are well known.

The zeolites are porous materials with the pores having generally uniform molecular dimensions. Cavities or cages are formed in the zeolite and are connected by channels of generally defined diameter. For the practice of this invention the cage diameter should be sufficiently large to permit the molecules to effectively enter the interior of the alumino-silicate for reaction and to exit as final product. Typically the pore size will range from about 6 to 15 Angstroms but the size of the pore required can vary depending upon the product being produced.

Molecular sieves have been developed which have been defined as nonzeolites but perform similarly in some reactions to zeolitic materials. They have a cage structure and typically contain alumina and silica in combination with other components, e.g., phosphorus, titania, etc. Representative crystalline molecular sieves are described in U.S. Pat. No. 4,440,871, European patent No. 124119 and European patent No. 121232 and are incorporated by reference. For purposes of this invention, these molecular sieves are deemed equivalent to and are to be included within the term crystalline molecular sieves.

Other nonalumino-silicate zeolites which can be used in the practice of the invention are the boron containing zeolites, e.g., borosilicates and borogermanates.

Sufficient alkali metal must be exchanged with appropriate acidic cations to render the crystalline molecular sieve acidic as defined by an acidity factor. This factor is determined by an ammonia absorption/desorption technique which involves treating the catalyst with ammonia at room temperature and then desorbing by heating to a temperature from ambient to 200° C. at 10°/minute, then holding at 200° C. for 2 hours. The amount of ammonia irreversibly adsorbed at 200° C. is indicative of acidity and indicative of the strength of the amine/acid bond. An acidity factor of 0.30 millimoles ammonia irreversibly adsorbed per gram of catalyst at 200.C. is usually necessary to obtain high catalytic activity.

The alkylation of the aromatic amines to effect ring alkylation of the aromatic amine can be carried out in a fixed bed reactor with the reactants being fed downflow or upflow through the reactor. The reaction can also be carried out in a stirred autoclave. Temperatures from 100 to 250° C., preferably 150-220° C. and pressures of from 50 to 3000 psig, preferably 250-1500 psig are utilized.

One of the problems associated with the utilization of a highly acidic crystalline alumino-silicate as a catalyst for the alkylation of toluenediamine and para-phenylenediamine with isobutylene as the alkylating reagent is that the catalyst deactivates rapidly. The reaction profile is such that the catalyst is extremely active and selective under initial operating conditions but deactivates quickly to a point where the catalyst must be regenerated. Process control becomes extremely difficult over time. The exact mechanism of deactivation is not fully understood, but it is believed there may be some polymerization of the olefin, formation of tars from by-products or impurities in the toluenediamine or para-phenylenediamine feedstock, reduced solubility of the alkylated aromatic diamine in the feed, or amine salt formation. Nonetheless the catalyst must be frequently regenerated if process control is to be maintained. In contrast, such catalysts used in the alkylation of other aromatic amines e.g., aniline or meta-phenylenediamine with $C_{2-4}$ olefins, such as propylene, do not deactivate nor does deactivation of the catalyst occur in the alkylation of toluenediamine with propylene.

It has been found, in contrast to some reactions associated with the alkylation of aromatic amines, that the addition of water to the reaction zone enhances catalyst life without substantially and adversely affecting conversion or selectivity. Sufficient water is added to the catalyst to effect at least partial saturation of the catalyst during contact with the aromatic diamine and olefin and then it should be periodically contacted with small amounts of water during the reaction. When operating in a batch mode, water can be added prior to charging the reactants to the reactor or water can be added to the reactor. Saturation or equilibration can be determined by conventional techniques; however, water contents of from about 1 to 30% by weight of the catalyst, i.e., a crystalline alumino-silicate catalyst can be utilized without sacrificing activity. Water can be added with the catalyst or it can be injected into the reactor. Injection is particularly suited for fixed bed operation. If injected during fixed bed operation, from about 0.5 to 10% water by weight based upon aromatic amine is required. Optimum amounts may be determined by monitoring the reaction profile. To optimize water addition in the process, conversion of the aromatic amine to desired product should be monitored. Too much water may cause conversion to decrease as will too little water. The former is due to reaction interference and the latter to catalyst deactivation.

The following examples are provided to illustrate various embodiments of the invention and are not intended to restrict the scope thereof.

EXAMPLE 1

Preparation of tert-butyl toluenediamine

Several runs were made producing tert-butyl-toluenediamine. In the initial run 40 pounds (0.32 moles) of 80% 2,4-toluenediamine and 20% 2,6-toluenediamine were charged to a 16-gallon reactor equipped with an agitator and capable of withstanding pressures of 900 psig. Then approximately 8 pounds of catalyst, the catalyst being an H-Y zeolite (pellets sold under the trademark LZ-y82) were charged to the reactor. For the first charge, the catalyst was exposed to the atmosphere and allowed to equilibrate to a level of about 24% water. The reactor was sealed, pressurized and then depressurized with nitrogen in order to remove all of the air from the system. Then, the contents were heated to approximately 300° F. and agitation was commenced. Isobutylene was added to the reactor until the pressure reached 700 psig at which time the temperature was adjusted to 360° F. Additional isobutylene was added to the reactor to maintain reactor pressure between 750 to 900 psig over a 10-hour interval. After such time, the heating was stopped and the reactor was cooled to 150° F. Isobutylene was recovered from the product; 55 pounds of crude product containing unreacted toluenediamine, N-tert-butyl- toluenediamine; tert-butyl-toluene di-tert-butyl-toluenediamine and others was obtained. The crude product was withdrawn through a tube having a filter screen in the end of it; the catalyst remained in the reactor. Subsequent runs were conducted by recharging the reactor with toluenediamne and 800 ml of water or 22% water based on the catalyst. After each run the product was analyzed and conversion calculated showing the effect of water addition on catalyst life. Table 1 provides analytical data for the sets of results.

The procedure described above was repeated except that no water was added to the catalyst prior to or during each run. The initial catalyst was estimated to contain 2-4% water. Results are also set forth in Table 1.

TABLE I

Effect of Water on Catalyst Life tert-butyl-toluenediamine

| Run | % Water | % Conversion | NTBTDA | TBTDA | DTBTA | Others |
|---|---|---|---|---|---|---|
| | | | | Selectivity Mole % | | |
| 1 | 24% | 68% | 14 | 81 | 3 | 2 |
| 2 | 800 ml | 61.1 | 15 | 76 | 7 | 2 |
| 3 | " | 58.1 | 17 | 78 | 4 | 1 |
| 4 | " | 54.6 | 19 | 77 | 4 | — |
| 5 | " | 51.5 | 19 | 77 | 4 | — |
| 6 | " | 50 | 19 | 78 | 3 | — |
| Comparison No Water Added | | | | | | |
| 1A | 2-4% | 68 | | | | |
| 2A | No | 57 | | | | |
| 3A | Water | 49 | | | | |
| 4A | Added | 33 | | | | |
| 5A | | 26 | | | | |

NTBTDA refers to N-tert-butyl-toluenediamine.
TBTDA refers to an 80-20 isomer mix of 5-tert-butyl-2,4-toluenediamine and 3-tert-butyl-2,6-toluenediamine.
DTBTDA refers to 3,5-di-tert-butyl-2,6-toluenediamine; N,N and N-ring di-tert-butyl-toluenediamine.

Conversion and selectivity were measured for the first series of runs, i.e., runs 1-6 wherein the catalyst was saturated with water to a level of about 24% by weight and then increments of water added to provide about 22% water by weight of the catalyst prior to each charge. Conversion remained high through the first six runs, and selectivity to TDA remained high. During the second series of runs 1A-5A the catalyst was only exposed to the atmosphere and no attempt was made to saturate the catalyst with water; then no water was added during subsequent runs. It should be noted conversion decreased. This deactivation decrease makes the separation of the reaction product more difficult, particularly for process control. Selectivities were not provided in Runs 1A-5A in view of the differences in conversion versus number of runs made.

EXAMPLE 2

Preparation of tert-butyl-para-phenylenediamine (PPD)

Several runs were made to produce tert-butyl-para-phenylenediamine with the alkylation of para-phenylenediamine (PPD) being carried out in a manner similar to Example 1, except that the reactions were carried out in a 1 liter reactor. Approximately 43 grams of the H-Y LZ-Y82 zeolite pellets were charged to the reactor followed by the addition of 216 grams of PPD. The PPD amine and the catalyst were heated to a temperature of about 180° F. to melt the material. At that time, 224 grams of isobutylene and water, in the amounts indicated, were charged to the reactor. The contents were heated to 340° F., and the temperature adjusted to the run conditions of 380 F. for a period of 10 hours. Pressure in the reactor at the initial time of reaction was about 900 to 1,000 psig and then decreased as the isobutylene was consumed. At the end of the 10-hour reaction period, the reactor contents were cooled and removed.

Table 2 sets forth the reaction conditions and results where no water was added.

Table 3 shows the influence of water addition.

TABLE 2

T-Butyl para-phenylenediamine no water added

| Run | 1 | 2 | 3 | 4 |
|---|---|---|---|---|
| $H_2O$ | 0 | 0 | 0 | 0 |
| % Conv. PPD | 65.1 | 57.4 | 20.3 | 17.6 |
| Selectivity Mole Percent to: | | | | |
| NTBPPD | 36.6 | 40.8 | 43.7 | 54.7 |
| 3TBPPD | 59.6 | 56.1 | 53.8 | 45.3 |
| DTBPPD | 3.8 | 3.1 | 2.5 | 0.0 |

NTBPPD refers to N-tert-butyl-para-phenylenediamine;
3TBPPD refers to 3-tert-butyl-para-phenylenediamine;
DTBPPD refers to 2,5-di-tert-butyl-para-phenylenediamine.

TABLE 3 tert-Butyl Para-phenylenediamine

| Runs | 1 | 2 | 3 | 4 | 5 | 6 | 7 | 8 | 9 | 10 | 11 | 12 | 13 |
|---|---|---|---|---|---|---|---|---|---|---|---|---|---|
| $H_2O$ Added | 0 | 20 | 0 | 20 | 0 | 20 | 0 | 20 | 0 | 20 | 0 | 20 | 0 |
| Conversion PPD | 49.5 | 28.2 | 51.3 | 44.5 | 53.6 | 41.3 | 62.8 | 53.7 | 22.7 | 28.6 | 38.5 | 30.3 | 35.4 |
| Selectivity in mole % to: | | | | | | | | | | | | | |
| NTBPPD | 26.6 | 27.5 | 39.9 | 35.6 | 31.0 | 36.2 | 36.8 | 43.1 | 36.6 | 25.9 | 41.0 | 44.8 | 42.9 |
| TBPPD | 70.6 | 69.9 | 57.6 | 61.0 | 65.1 | 60.3 | 61.3 | 55.2 | 62.4 | 71.7 | 57.3 | 54.0 | 55.2 |
| ΣDTBPPD | 3.4 | 2.6 | 2.5 | 3.4 | 3.9 | 3.5 | 1.9 | 1.7 | 1.0 | 2.4 | 1.7 | 1.2 | 0.9 |

From the above data the initial runs show declining reactivity when water was added to the reaction and then an overall leveling out after run 7 although at somewhat lower conversion levels. Without water addition deactivation of the H—Y zeolite occurred as noted in Table 2. Thus, the data show that water delays deactivation of the catalyst.

EXAMPLE 3

Preparation of tert-butyl-meta-phenylenediamine (MPD)

The procedure of Example 2 was repeated, except that MPD was substituted for PPD. Table 4 sets forth the reaction conditions and results.

TABLE 4 tert-Butyl meta-phenylenediamine

| Runs | 1 | 2 | 3 | 4 | 5 | 6 | 7 | 8 | 9 | 10 | 11 | 12 | 13 | 14 | 15 | 1 |
|---|---|---|---|---|---|---|---|---|---|---|---|---|---|---|---|---|
| 20% $H_2O$ Added | 0 | 0 | 0 | 0 | + | + | 0 | 0 | 0 | 0 | 0 | 0 | 0 | 0 | 0 | |
| % Conversion MPD | 68.5 | 63.2 | 63.5 | 62.4 | 60.1 | 51.4 | 60.6 | 64.2 | 60.9 | 59.7 | 56.2 | 58.4 | 58.6 | Run Aborted Agitator Not Working | 65.4 | 62 |
| Selectivity in mole percent to: | | | | | | | | | | | | | | | | |
| NTBMPD | 16.6 | 17.6 | 21.1 | 18.2 | 19.6 | 19.2 | 17.3 | 19.9 | 16.0 | 19.6 | 20.7 | 18.3 | 21.3 | | 15.6 | 19 |
| TBMPD | 82.2 | 79.0 | 77.9 | 78.7 | 77.8 | 75.3 | 77.6 | 76.6 | 80.0 | 77.3 | 76.8 | 78.4 | 76.2 | | 79.8 | 78 |
| EDTBMPD | 1.2 | 3.4 | 1.0 | 3.1 | 2.6 | 5.5 | 5.1 | 3.5 | 4.0 | 3.1 | 3.5 | 3.3 | 2.5 | | 4.6 | 2 |

+ = 20% water based on weight of catalyst added. The results show that rapid catalyst deactivation did not occur in the ation of MPD at rates that were exhibited by PPD (Table 2). Water addition appeared to have little to no effect since deactivation was so slight.

EXAMPLE 4

Preparation of Cyclopentenyl meta-phenylenediamine (CPMPD)

The procedure of Example 3 was repeated, except that cyclopentadiene was substituted for isobutylene. In the first series of runs, no water was added to the reaction medium, and in the following sequence of runs, water was added in an amount to provide about 20% by weight of the catalyst. Table 5 presents these results.

TABLE 5

Cyclopentenyl meta-phenylenediamine
No Water Added

| Run | % $H_2O$ Added | % Conversion of MPD |
|---|---|---|
| 1 | 0 | 31 |
| 2 | 0 | 21 |
| 3 | 0 | 23 |
| Water Added | | |
| 1 | + | 38 |
| 2 | + | 19 |
| 3 | + | 18 |

TABLE 5-continued

Cyclopentenyl meta-phenylenediamine
No Water Added

| Run | % $H_2O$ Added | % Conversion of MPD |
|---|---|---|
| 4 | + | 16 |
| 5 | + | 13 |

+ = represents water addition in amount of 20% by weight of catalyst.

From the above data, it is noted that conversion of MPD decreased in the alkylation reaction with cyclopentadiene and the catalyst did not respond to the addition of water.

EXAMPLE 5

Preparation of tert-Butyl-toluenediamine via Fixed Bed Reactor

A commercial H-Y zeolite (catalyst base LZ-Y82 powder, manufactured by Union Carbide) was used without any pretreatment. The catalyst base LZ-Y82 is an ammonium exchanged powder form of a thermally-stabilized Linde type Y molecular sieve. It has a low level of sodium cations and excellent hydrothermal stability.

The catalyst was obtained as a powder which was pelletized in a press and then crushed and sieved to yield 12-18 mesh particles. Fifteen grams of this material were packed between retaining quartz beds in a stainless steel (SS-316) reactor tube of 0.44 inches internal diameter and 36 inches in length.

The toluenediamine (TDA)-isobutylene alkylation reaction was conducted in a continuous flow isothermal mode with downflow of the reactants. The TDA isomer used in the reaction was 2,4-TDA. More specific procedures used in the experiment are outlined below.

The reactor tube was heated to about 125° C. under nitrogen, and then molten TDA at about 130° C. was introduced. After the passage of a sufficient amount of TDA through the reactor, the flow of isobutylene was started to maintain a molar ratio of isobutylene (R) to TDA (R/N ratio) of about 1.2:1. The temperature was maintained at about 125° C. until the mixture of TDA and isobutylene flowed through the entire catalyst bed after which the temperature was increased in stages to the desired value of 180° C. Table 6 sets forth conditions and results.

TABLE 6

2,4-TDA/Isobutylene Alkylation Over LZ-Y82
Bases: Catalyst - 15 g LZ-Y82
T~180° C.
P~550 psig
R/N~1.3

| Time On Stream (h) | WHSV[1] (h$^{-1}$) | TDA Conversion (%) | Molar Selectivities (%)[2] | | |
|---|---|---|---|---|---|
| | | | TBTDA | NTBTDA | DTBTDA |
| 22 | 0.50 | 59 | 85.2 | 13.1 | 1.6 |
| 78 | 0.40 | 32 | 74.3 | 25.4 | 0.2 |
| 127 | 0.40 | 28 | 71.9 | 27.9 | 0.2 |
| 145 | 0.21 | 33 | 73.8 | 25.9 | 0.3 |

[1]WHSV is the weight hourly space velocity defined as g TDA per g catalyst per hour.
[2]TBTDA denotes monotertiarybutyl TDA which consists of 5-tertiarybutyl-2,4-TDA. NTBTDA denotes N-monotertiarybutyl TDA which consists of 2N-tertiarybutyl-2,4-TDA and 4N-tertiarybutyl-2,4-TDA. DTBTDA denotes ditertiarybutyl TDA which consists of 2N,5-ditertiarybutyl-2,4-TDA, 4N,5-ditertiarybutyl-2,4-TDA, and 2N,4N-ditertiarybutyl-2,4-TDA.

From the above data, deactiation occurred in the alkylation of 2,4-TDA with isobutylene via fixed bed. At 127 hours when conversion had dropped to about 28%, an attempt to increase conversion or activation of the catalyst by reducing TDA flow was made. That adjustment was unsuccessful in that conversion increase was minimal.

EXAMPLE 6

Prep of tert-Butyl 2,4 TDA with Water Addition

The procedure of Example 5 was repeated except that water was added to the reactor as indicated. Table 7 sets forth conditions and results.

TABLE 7

2,4-TDA/Isobutylene Alkylation over LZ-Y82
Bases: 9.5 g LZ-YB2
T~180° C.
P~575 psig
R/N~1.5

| Time On Stream (hr) | Water/TDA Molar Ratio | WHSV (hr$^{-1}$) | TDA Conversion (%) | Molar Selectivities (%) | | |
|---|---|---|---|---|---|---|
| | | | | TBTDA | NTBTDA | DTBTDA |
| 26 | 0 | 0.43 | 62 | 82.4 | 15.6 | 1.9 |
| 73 | 0 | 0.39 | 30 | 72.2 | 27.6 | 0.2 |
| 73 | Start H$_2$O Cofeed | — | — | — | — | — |
| 170 | 1.6 | 0.43 | 37 | 80.7 | 17.3 | 2.1 |
| 214 | Stop H$_2$O Cofeed | — | — | — | — | — |
| 236 | 0 | 0.26 | 65 | 82.5 | 12.8 | 4.7 |

The results show at 73 hrs. conversion had dropped to 30% and that catalyst deactivation had occurred. Catalyst activity increased slightly with water addition and then greatly when terminated. Space velocity was also decreased. Continuous feed of water would be expected to retard deactivation.

EXAMPLE 7

Prep of tert-Butyl 2,4 TDA with Water Addition

The procedure of Example 6 was repeated except that water was added incrementally over time and at various levels based on TDA. Table 8 sets forth conditions and results.

TABLE 8

2,4-TDA/Isobutylene Alkylation over LZ-Y82
Bases: 17.9 g LZ-Y82
T~180° C.
P~550 psig
R/N~1.3-1.8

| Time On Stream (h) | Water/TDA Molar Ratio | WHSV (h$^{-1}$) | TDA Conversion (%) | Molar Selectivities (%) | | |
|---|---|---|---|---|---|---|
| | | | | TBTDA | NTBTDA | DTBTD |
| 24 | 0.35 | 0.24 | 57 | 82.7 | 12.6 | 4.7 |
| 65 | 0.32 | 0.26 | 52 | 83.8 | 13.7 | 2.6 |
| 185 | 0.35 | 0.24 | 42 | 81.7 | 16.9 | 1.5 |
| 302 | 0.32 | 0.26 | 39 | 81.3 | 17.8 | 0.9 |
| 302 Water Flow Stopped | | | | | | |
| 323 | 0 | 0.27 | 41 | 79.4 | 20.2 | 0.4 |

TABLE 8-continued

| 2,4-TDA/Isobutylene Alkylation over LZ-Y82 Bases: 17.9 g LZ-Y82 T~180° C. P~550 psig R/N~1.3-1.8 | | | | | | |
|---|---|---|---|---|---|---|
| Time On Stream (h) A | Water/TDA Molar Ratio | WHSV (h$^{-1}$) | TDA Conversion (%) | Molar Selectivities (%) | | |
| | | | | TBTDA | NTBTDA | DTBTD |
| 347 | 0 | 0.27 | 33 | 75.8 | 23.9 | 0.3 |
| 364 | 0 | 0.26 | 32 | 74.5 | 25.2 | 0.3 |
| 364–383 Regeneration by water | | | | | | |
| 406 | 0 | 0.30 | 42 | 80.6 | 18.4 | 0.9 |
| 429 | 0 | 0.31 | 21 | 67.8 | 31.9 | 0.3 |
| 431 Water cofeed started at H$_2$O/TDA molar ratio≃0.3 | | | | | | |
| 501 | 0.26 | 0.24 | 34 | 76.8 | 22.7 | 0.5 |
| 502 H$_2$O/TDA molar ratio increased≃1.7 | | | | | | |
| 519 | 1.77 | 0.29 | 32 | 82 | 16.7 | 1.4 |
| 547 H$_2$O/TDA molar ratio decreased to≃0.3 | | | | | | |
| 569 | 0.20 | 0.28 | 50 | 83.2 | 15.1 | 1.7 |
| 689 | 0.32 | 0.25 | 44 | 82.4 | 16.7 | 0.9 |
| 782 | 0.24 | 0.25 | 41 | 80.3 | 18.8 | 0.9 |

The above data show the maintenance in catalyst activity alternatively or deactivation of the catalyst retarded on water addition from 24–302 hr. stream time (compared with Example 5). On termination of water feed at 323 to 431 hours, there was a slight increase and subsequent decrease in catalyst activity. When water levels were decreased to 0.3 moles/mole TDA activity increased showing perhaps water addition may have been on the high side at the 519 hour period.

What is Claimed is:

1. In a process for producing ring alkylated toluenediamine and para-phenylenediamine amines by the reaction of said amines with isobutylene in the presence of an acidic crystalline alumino-silicate catalyst, the improvement for retarding catalyst deactivation in the ring alkylation of said amines which comprises contacting the catalyst with water in an amount sufficient for retarding deactivation of the catalyst but insufficient for substantially retarding the reaction.

2. The process of claim 1 wherein the aromatic amine is toluenediamine.

3. The process of claim 2 wherein the mole ratio of isobutylene to toluenediamine is from about 2 to 4:1.

4. The process of claim 1 wherein the water is added in an amount of from about 1 to 30% by weight of the catalyst.

5. The process of claim 4 wherein a reaction temperature ranges from 150 to 220° C. and a reaction pressure ranges from 50 to 3000 psig.

6. The process of claim 4 wherein water is added periodically to the alkylation reaction.

7. In a process for the production of ring alkylated aromatic amine by the reaction of toluenediamine and para-phenylenediamine with a isobutylene in a fixed bed catalytic reaction zone using a crystalline alumino-silicate as the catalyst, the improvement which comprises:
incorporating a sufficient amount of water to the reaction zone to substantially retard deactivation of the crystalline alumino-silicate catalyst but insufficient for retarding the reaction.

8. The process of claim 7 wherein the mole ratio of isobutylene to toluenediamine and para-phenylenediamine is from about 2–4:1.

9. The process of claim 8 wherein from 0.5 to 10% water is added to the reaction zone based upon the weight of aromatic amine fed to the reaction zone.

10. The process of claim 9 wherein the reaction temperature ranges from 150 to 220° C. and the pressure ranges from 500 to 1500 psig.

11. The process of claim 10 wherein said amine is toluenediamine.

12. The process of claim 9 wherein the water is added incrementally to the reaction zone.

* * * * *